United States Patent
Amblard et al.

(10) Patent No.: US 7,164,946 B2
(45) Date of Patent: Jan. 16, 2007

(54) AUTOMATIC SWITCHING OF DDD/AAI MODE PACING FOR AN ACTIVE IMPLANTABLE MEDICAL DEVICE SUCH AS PACEMAKER, DEFIBRILLATOR AND/OR CARDIOVERTOR

(75) Inventors: Amel Amblard, Chatenay-Malabry (FR); Marcel Limousin, Paris (FR)

(73) Assignee: Ela Medical S.A.S., Montrouge (FR)

( * ) Notice: Subject to any disclaimer, the term of this patent is extended or adjusted under 35 U.S.C. 154(b) by 468 days.

(21) Appl. No.: 10/394,408

(22) Filed: Mar. 20, 2003

(65) Prior Publication Data

US 2004/0010292 A1    Jan. 15, 2004

(30) Foreign Application Priority Data

Mar. 22, 2002   (FR) .................................. 02 03606

(51) Int. Cl.
*A61N 1/362*    (2006.01)
(52) U.S. Cl. .............................................. 607/9; 607/4
(58) Field of Classification Search ..................... 607/9
See application file for complete search history.

(56) References Cited

U.S. PATENT DOCUMENTS

| | | | | |
|---|---|---|---|---|
| 5,133,350 | A * | 7/1992 | Duffin | 607/6 |
| 5,318,594 | A | 6/1994 | Limousin et al. | 607/9 |
| 5,893,882 | A | 4/1999 | Peterson et al. | 607/14 |
| 5,928,271 | A | 7/1999 | Hess et al. | 607/14 |
| 6,078,836 | A | 6/2000 | Bouhour et al. | 607/14 |
| 6,122,546 | A * | 9/2000 | Sholder et al. | 607/9 |
| 6,397,105 | B1 * | 5/2002 | Bouhour et al. | 607/9 |
| 6,772,005 | B1 * | 8/2004 | Casavant et al. | 607/4 |

2002/0082646 A1    6/2002   Casavant et al.

FOREIGN PATENT DOCUMENTS

| | | |
|---|---|---|
| EP | 0 488 904 A1 | 6/1992 |
| WO | WO 99/10044 * | 3/1999 |
| WO | WO 01/70104 A2 | 9/2001 |

\* cited by examiner

*Primary Examiner*—George Manuel
*Assistant Examiner*—Nicole R. Kramer
(74) *Attorney, Agent, or Firm*—Orrick Herrington & Sutcliffe, LLP

(57) ABSTRACT

An active implantable medical device for cardiac rhythm management, such as a pacemaker, defibrillator, and/or cardioverter, having an improved DDD/AAI operating mode that automatically switches between operating in an AAI and a DDD pacing mode for cardiac rhythm management. This device includes atrial and ventricular detection and stimulation circuits. It can function in a DDD pacing mode or an AAI pacing mode with ventricular detection. The commutation of an AAI pacing mode towards a DDD pacing mode occurs when one of the following conditions is met: (i) the number of consecutive atrial events detected, not followed by a ventricular detection, exceeds an authorized number, for example 2 events; (ii) the number of non-consecutive atrial events not followed by a ventricular detection exceeds an authorized number over the duration of a monitoring window extending over a third number of given consecutive atrial events, for example, 3 events out of 12; (iii) the number of atrial events followed by a ventricular detection occurring after a delay is longer than one predetermined duration exceeds an authorized value, for example, six events for a 300 ms delay; or (iv) the interval separating two ventricular events exceeds an authorized predetermined delay, for example, 3 seconds. Atrial extrasystoles are not counted as atrial events.

28 Claims, 2 Drawing Sheets

FIG_1
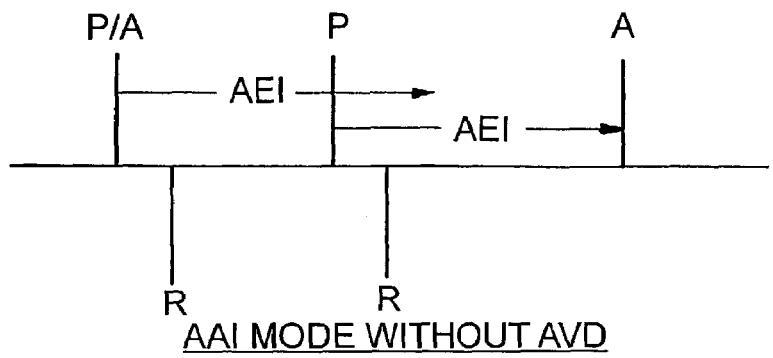
AAI MODE WITHOUT AVD
FIG_2
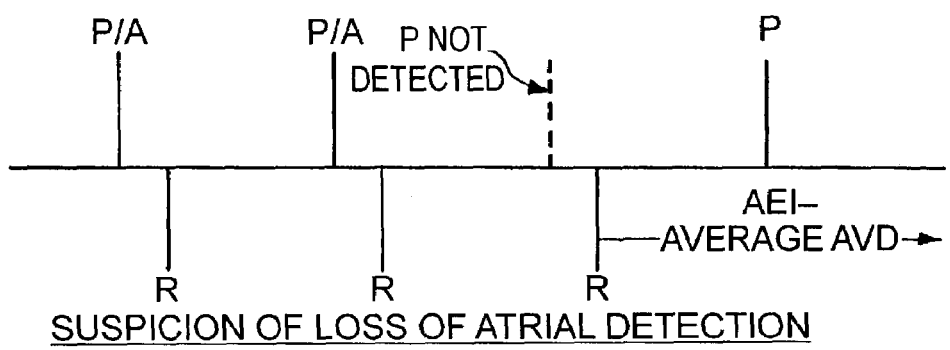
SUSPICION OF LOSS OF ATRIAL DETECTION
FIG_3
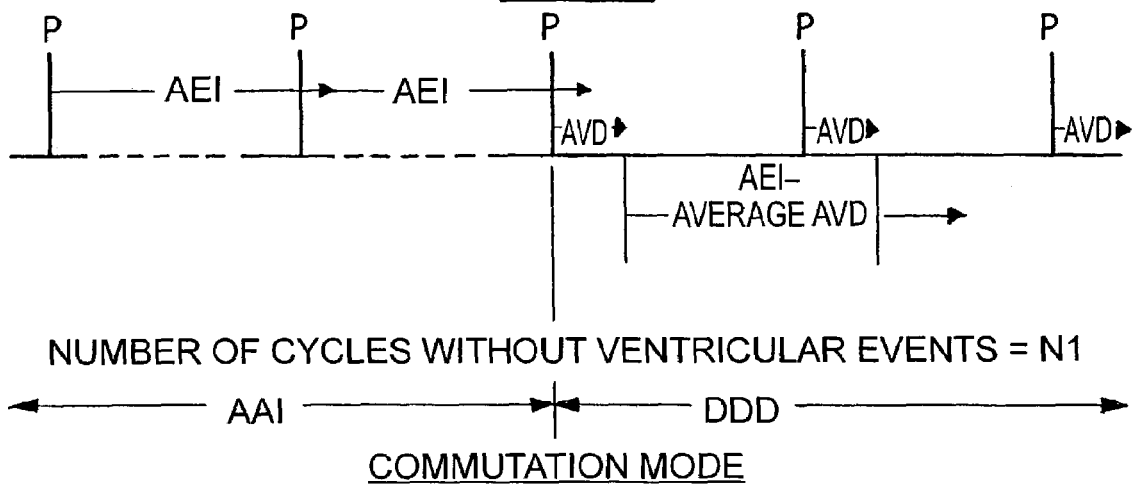
NUMBER OF CYCLES WITHOUT VENTRICULAR EVENTS = N1
COMMUTATION MODE

FIG_4
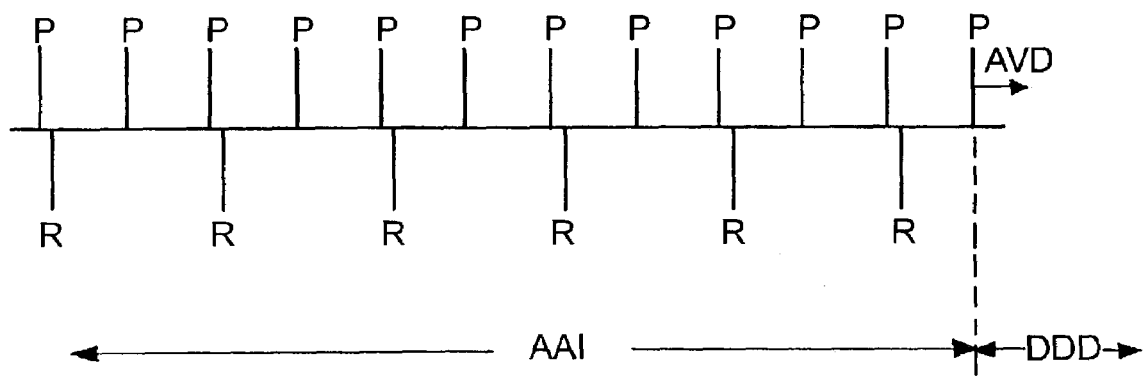
FIG_5
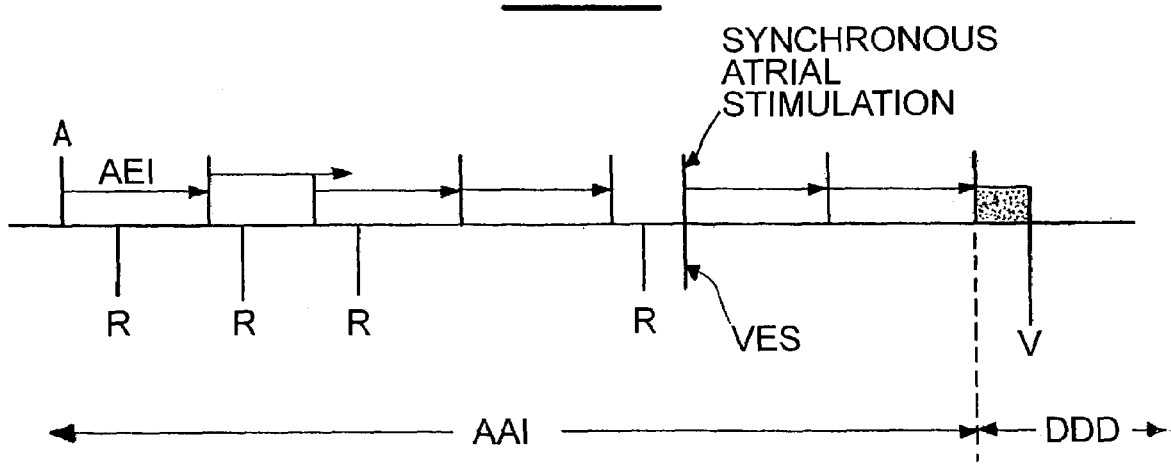

AUTOMATIC SWITCHING OF DDD/AAI MODE PACING FOR AN ACTIVE IMPLANTABLE MEDICAL DEVICE SUCH AS PACEMAKER, DEFIBRILLATOR AND/OR CARDIOVERTOR

FIELD OF THE INVENTION

The present invention relates to "active implantable medical devices" as such devices are defined by the Jun. 20, 1990 directive 90/385/CEE of the Counsel of the European Communities, and more particularly to pacemaker, "multisite" (triple or quadruple chamber), defibrillator and/or cardiovertor devices that are able to deliver to the heart stimulation pulses of low energy for the treatment of the disorders of the heartbeat, and even more particularly to those devices that include stimulation and detection circuits associated with the atrium and the ventricle, that can operate according to two known operating modes, DDD and AAI pacing modes (the AAI mode being a DDD mode having a lengthened atrio-ventricular delay), and that are equipped with a mode called "DDD-AMC" ensuring an automatic mode commutation (AMC) mode from DDD to AAI pacing modes and conversely. The term "AMS", referring to automatic mode switching, has the same meaning as AMC.

BACKGROUND OF THE INVENTION

The basic operating pacing mode of a DDD/AAI pacemaker is an AAI pacing mode, with a single chamber atrial stimulation, together with and a contemporaneous monitoring (detection) of the ventricular activity. This AAI pacing mode is maintained as long as atrio-ventricular conduction is normal, i.e., as long as each atrial event (either an atrial detection or P-wave, corresponding to a spontaneous activity, or an atrial stimulation, or A-wave) is followed by an associated ventricular detection (a spontaneous activity or an R-wave).

In certain circumstances, however, atrio-ventricular blocks (AVB) can appear that are known as "paroxystic", i.e., involving a temporary defect of the conduction that should lead to a spontaneous depolarization of the ventricle. In this case, the pacemaker commutes automatically to the DDD pacing mode, with cardiac rhythm management parameters that are optimized for this situation of temporary AVB. After disappearance of the AVB, and there is a re-establishment of spontaneous atrio-ventricular conduction, and, when a certain number of conditions are filled, the pacemaker turns again automatically to the AAI pacing mode (with ventricular surveillance).

A known DDD-AMC system for the automatic commutation of between DDD and AAI pacing modes is described, for example, in EP-A-0 488 904 and its counterpart U.S. Pat. No. 5,318,594) (commonly assigned herewith to ELA Médical), the disclosure of which U.S. Pat. No. 5,318,594 is incorporated by reference herein in its entity.

These automatic mode switching devices can be in particular implanted among patients that are suffering from sinusal dysfunctions that are likely to produce disorders or troubles of the atrial rate. The term "trouble of the atrial rate" or "TdAR" is a generic term that cover various atrial arrhythmias (non physiological episodes of acceleration of the rate) such as tachycardia, fibrillation, flutter, etc; troubles that are all characterized by the detection of a fast atrial rate. Primarily, one will consider that there is TdAR when the detected atrial rate exceeds an acceptable threshold level, this threshold level being eventually related to a degree of effort determined by a physiological sensor.

To reduce the episodes of atrial arrhythmia, the pacemaker can be equipped with a mode called "overdrive", which is a particular mode ensuring an atrial stimulation at a frequency that is slightly higher than the subjacent natural rate. This mode of overdrive is described, for example, in European publication EP-A-0 880 979 and its corresponding U.S. Pat. No. 6,078,836 (commonly assigned herewith to ELA Médical).

The starting point of the present invention lies in a certain number of observations carried out at the time of a clinical follow-up of patients implanted with devices able to implement the two above mentioned functionalities, namely DDD-AMC and overdrive.

Indeed, the DDD-AMC mode of stimulation is reserved to the patients presenting a normal atrio-ventricular conduction. In this stimulation mode, the pacemaker calculates an atrial ventricular delay ("AVD") of stimulation and detection by analyzing the spontaneous conduction of the patient. This principle of operation authorizes, in the majority of times, the maintenance of a spontaneous ventricular activity. However, this behavior principle is limited by a maximum duration of the conduction delay, about 300 ms after an atrial detection, and 350 ms after an atrial stimulation.

This operating mode is adapted to those patients presenting a sinusal activity but, in the event of sinusal dysfunction requiring an atrial stimulation, it was noted that, on a significant number of cardiac cycles either (i) a ventricular stimulation was started, i.e., no ventricular activity was, or could, be detected, or (ii) a fusion occurred, i.e., a ventricular stimulation intervened in a concomitant way to a spontaneous ventricular depolarization, detected in the same temporal window as the ventricular stimulation. These phenomena are probably due to the fact that atrial stimulation increases the atrio-ventricular delay for conduction, which then exceeds the value of the programmed AVD, typically 350 ms after stimulation.

When one wants to combine the algorithms for the prevention and treatment of atrial arrhythmias with a DDD-AMC stimulation mode, one notes a very significant increase in the number of cycles with a ventricular stimulation. Indeed, the object of these algorithms is to remove the spontaneous atrial activity and to "overdrive" the sinus permanently.

It is also known that, to maximize the benefit of the overdrive algorithms in the prevention of atrial fibrillation ("AF"), it is significant to maintain good atrial hemodynamics. But a premature ventricular stimulation (which may occur because of a too short AVD), preventing the expression of spontaneous ventricular depolarization, modifies the atrio-ventricular sequence and loses the benefit of atrio-ventricular optimization such that, the atrium will not have time to fill (or to eject the blood) completely.

OBJECTS AND SUMMARY OF THE INVENTION

The invention proposes to resolve these noted difficulties while bringing an improvement to the known devices, for better associating prevention and treatment of the atrial arrhythmias with a DDD-AMC stimulation mode, by a suitable adjustment of this operating mode.

More precisely, it is an object of the present invention to propose a new mode of commutation (switching) allowing, as in the case of the known DDD-AMC stimulation mode (for example the mode described in the above-mentioned EP-A-0 880 979 and U.S. Pat. No. 6,078,836), an automatic commutation between DDD and AAI pacing modes, but in which the AAI pacing mode will not be a DDD pacing mode including a lengthened atrio-ventricular delay. Essentially, the aim is that the device remains as long as possible in the AAI pacing mode, by delaying to the maximum the commutation to the DDD pacing mode, and authorizing an absence of ventricular activity during a predetermined, programmable number of cycles.

The type of device to which the invention applies is an active implantable medical device for cardiac rhythm management, in particular a pacemaker, a defibrillator and/or a cardiovertor, including means for detecting atrial and ventricular spontaneous events, means for stimulating the ventricle and the atrium, means for operating the device in the DDD pacing mode, means for operating the device in the AAI pacing mode with a ventricular detection, and a DDD/AAI stimulation mode for commuting the pacing modes, able to control the commutation of AAI pacing mode to the DDD pacing mode, and conversely, according to predetermined criteria. Suitable means for performing these functions are known in the art and may be discrete analog circuits, such as detection circuits or differential amplifiers, and pulse generator circuits, or a combination of such circuits and digital signal processing, using an analog-to-digital convertor, microcontroller/microprocessor, memory and software instructions. Exemplary representative structures are disclosed in U.S. Pat. Nos. 5,318,594 and 6,078,836, the disclosures of which are incorporated herein by reference in their entities.

In a manner characteristic of the invention, the means for commuting the modes controls the commutation of the AAI pacing mode towards the DDD pacing mode when at least one of the following conditions is fulfilled:

1) a number of consecutive atrial events that are not followed by a ventricular detection exceeds a first number, preferably two events;

2) the number of non-consecutive atrial events not followed by a ventricular detection exceeds a second number, preferably three events, over the duration of a monitoring window extending over a third number of consecutive atrial events, preferably twelve events;

3) the number of atrial events followed by a ventricular detection occurring after a delay longer than one predetermined duration exceeds a fourth number, preferably six events for a predetermined duration of (i) at least 300 ms in the event of an atrial detection, or (ii) at least 350 ms in the event of an atrial stimulation; and 4) the interval separating two ventricular events exceeds a predetermined delay, preferably three seconds.

The atrial extra systoles ("AES") events are preferably identified and are not to be counted as atrial events in the conditions above.

Conversely, the means for commuting the modes controls the commutation of the DDD pacing mode towards the AAI pacing mode when (i) the return of a spontaneous ventricular activity is detected over a number of consecutive cycles exceeding a fifth number, preferably twelve cycles, or (ii) after a number of ventricular events (stimulated or sensed events) exceeding a sixth number, preferably a hundred events.

In a preferred embodiment, the means for commuting the modes also operates to inhibit any commutation of mode, and to force the operating mode to a DDD pacing mode when, during a first predetermined lapse of time, the number of commutations of AAI towards DDD exceeds a seventh number, preferably fifteen commutations during twenty-four hours, or when, during a second duration the frequency of the commutations exceeds an eighth number, preferably five commutations per day, over three days.

Preferably, the device can also include means for detecting ventricular extrasystoles ("VES"), and means for delivering a synchronous atrial stimulation in the event of detected ventricular extrasystole, independently of operating in the AAI or DDD pacing modes.

BRIEF DESCRIPTION OF THE DRAWINGS

Further features, benefits and characteristics of the invention will become apparent to a person of ordinary skill in the art from the following description, made with reference to the annexed figures, in which FIGS. 1 to 5 are chronograms corresponding to the various operating modes of a device in accordance with a preferred embodiment of the invention.

DETAILED DESCRIPTION OF THE INVENTION

The invention is preferably implemented by suitable programming of the control software of a microprocessor-controlled pacemaker of the known double chamber type, integrating on the one hand a conventional DDD pacing mode, and on the other hand a conventional AAI pacing mode with a contemporaneous monitoring of the ventricular activity. The programming is believed to be within the abilities of a person of ordinary skill in the art of designing pacemakers.

One will first provide the following definitions that are used in the following description.

"Detection P": sensing of a spontaneous activity having its origin in the atrium; it will be considered that there is indeed a detection P if the detected event is not followed, within a given delay, for example, within 31 ms, by a ventricular detection. This given delay characteristic allows for identifying an event as a "far-field ventricular" event, i.e., sensing an event in the atrium that is a consequence of a remote depolarization coming from the ventricle.

"Detection R": sensing of a spontaneous activity having its origin in the ventricle.

"Stimulation A": stimulation delivered in the atrium.

"Stimulation V": stimulation delivered in the ventricle.

"Atrial event": a detection P or a stimulation A event;

"Ventricular event": a detection R or a stimulation V event;

"Cardiac cycle": an interval of time separating two events of comparable nature in the same cavity, for example, a period separating two detections P, or two stimulations A.

"Average PP": an average interval of the atrial rate, calculated, for example, over eight cardiac cycles not including an extrasystole.

"Escape Interval (EI)": an interval of time, counted after a detection or a stimulation in a given cavity, at the end of which a stimulation is delivered within the given cavity if no spontaneous event is detected in the given cavity. For the atrium, it is the Atrial Escape Interval (AEI).

"Atrial extrasystole (AES)": an atrial detection occurring inside the post-atrial, atrial refractory period ("PAARP"), the calculation of the PAARP being that for a standard pacemaker of the DDD type.

"Ventricular extrasystole (VES)": a ventricular detection is a VES when it is preceded by a ventricular detection or stimulation, and when the coupling interval (R-R interval or V-R interval) is less than or equal to a programmable value, for example, 75%, of the average PP.

For further details on the detection and the treatment of the extrasystoles, one will be able to refer to European publication EP-A-0 550 342 and its corresponding U.S. Pat. No. 5,312,451, (commonly assigned herewith to Ela Médical), which describes a suitable algorithm for the detection and treatment of VES by an asynchronous stimulation of the atrium and a controlled stimulation of the ventricle.

For the implementation of the invention, a certain number of functions typically found in dual chamber pacemakers, if they are present, are maintained as they are: thus, the pacing (stimulation) algorithms, the fallback algorithms, and the algorithms for the prevention of the so-called (pacemaker-mediated (PMT) or re-entrant tachycardias) algorithms are maintained, as also are those algorithms able to calculate and apply the PAARP periods and those that protect against a retrograde conduction in the event of a suspicion of VES.

With this background, the present invention in accordance with a preferred embodiment may be implemented in the following manner.

Initially, the pacemaker is operating in an AAI pacing mode with monitoring of the ventricular activity (See, chronogram of FIG. 1), i.e., an atrial detection (detection P), or an atrial stimulation (stimulation A) does not start an AVD delay, but instead starts an atrial escape interval AEI.

In this AAI pacing mode, the absence of ventricular activity is thus accepted for a given number N1 of cycles without causing delivery of a ventricular stimulation. This number N1 is preferably programmable, for example, N1=2 cycles (cf in particular the situation illustrated on the left part of the chronogram of FIG. 3).

In the event that there is a ventricular detection, this detection does not normally have an effect on the AEI, except in the event of a suspicion of a loss of atrial detection.

This case of suspicion of loss of atrial detection is illustrated by the chronogram of FIG. 2. The situation illustrated in FIG. 2 is that of a ventricular detection R that is not preceded by an atrial detection P (shown in phantom lines), and in the absence of an acceleration of the rate. An acceleration of the rate is detected when the coupling interval (interval R-R) crosses a predetermined threshold. In this case, the algorithm suspects not a VES (because in such a case there would have been an acceleration of the rate), but rather a defect of atrial detection, and starts again an Atrial Escape Interval having a value equal to AEI–average AVD.

As noted, the AAI pacing mode is one that also has a monitoring of the ventricular activity. The algorithm in addition seeks the presence or the absence of a ventricular event, which in the latter case could leave to a suspicion of AVB, so as to switch, if required, to the DDD pacing mode of double chamber stimulation with atrio-ventricular association, i.e., with a calculation and application of an AVD. This situation of mode commutation corresponds to the chronogram of FIG. 3.

Four criteria can be used to start the commutation of mode of AAI towards DDD:

1) the number of consecutive blocked atrial events (i.e., the number of atrial events not followed by a ventricular detection) is greater than the authorized programmable value N1 (for example, N1=2); or 2) the number of blocked atrial events is greater than an authorized programmable number N2 (for example, N2=3) during a monitoring window of N3 atrial events, N3 being a programmable number, for example, N3=12 events. (This situation is in particular illustrated on the chronogram of FIG. 4); or 3) the number of atrial events followed by a ventricular detection after an abnormally long programmable delay, for example, 300 ms is greater than an authorized programmable number N4, for example, N4=6 events; or 4) the ventricular pause (i.e., the interval separating two ventricular events) exceeds an authorized programmable delay, for example, 3 seconds.

In the presence of one of these criteria, the device commutes from the AAI pacing mode with ventricular surveillance to the DDD pacing mode with AVD. The values of AVD are either those initially programmed by the physician, or those automatically calculated by the algorithm (one will be able to refer in this respect to the above mentioned Ep-A-0 488 904 and U.S. Pat. No. 5,318,594). The AVD is activated on any atrial event that is not an AES, and the DDD pacing mode continues until the return of a spontaneous ventricular activity over a programmable number N5 of consecutive cycles, for example, N5=12 cycles, or after a programmable maximum number N6 of ventricular events, for example, N6=100 events.

The device then commutates from DDD to AAI and remains in the AAI pacing mode as long as none of the four above mentioned criteria of commutation of AAI towards DDD is again fulfilled.

In a preferred embodiment, it is desirable to envisage a limitation of the number of successive commutations of AAI towards DDD over a given period of time. For example: (i) if, over a period of 24 hours, the number of commutations exceeds a programmable maximum number N7 of times, for example, N7=15 times; or (ii) if, during three consecutive days, the daily number of commutations exceeds a programmable maximum number N8 of times, for example, N8=5 times, in each 24 hour period, then the device commutes definitively to the DDD pacing mode, with the values of AVD programmed in the factory or at the implantation, and remains in DDD until later reprogrammed by the physician.

In yet another preferred embodiment, the algorithm also manages the VES: In the event of a detected VES, a synchronous atrial stimulation is delivered by the device, whether the pacemaker is in a DDD pacing mode or an AAI pacing mode. This last situation is in particular illustrated on the chronogram of FIG. 5.

Suitable devices for which the present invention has application include, for example, the Defender™ and Alto™ brands of defibrillators and the Talent™ and Symphony™ brands of pacemakers available from Ela Médical, Montrouge France. These devices are microprocessor based systems having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits have inputs to connect to a lead that is in the desired cardiac chamber(s) that is used to detect the cardiac signals in the atrium and the ventricle, in the left and/or right chambers, as well as the pulse generating circuits having outputs used to deliver via leads low energy stimulation pulses to the cardiac chambers, are well known and any suitable design may be used.

One skilled in the art will appreciate that the present invention can be practiced by other than the described embodiments, which are presented for purposes of illustration and not of limitation.

We claim:

1. An active implantable medical device for cardiac rhythm management comprising:
   means for detecting spontaneous atrial and ventricular events,
   means for counting detected spontaneous atrial events;
   means for stimulating the ventricle and the atrium,
   means for operating the device in a DDD mode,
   means for operating the device in the AAI pacing mode with a ventricular detection, and
   means for commuting the mode between said DDD pacing mode and said AAI pacing mode according to a predetermined criteria, wherein said mode commuting means further comprises means for monitoring the following four conditions:
   a) a first counted number of consecutive detected sinus atrial events not followed by a detected spontaneous ventricular event that is greater than a first number (N1);
   b) a second counted number of non-consecutive detected sinus atrial events not followed by a detected spontaneous ventricular event that is greater than a second number (N2), said second counted number being counted during a monitoring window comprising a third number (N3) of consecutive detected sinus atrial events;
   c) a third counted number of detected atrial events followed by a detected spontaneous ventricular event occurring after a delay, said delay being greater than a first duration, said third counted number being greater than a fourth value (N4); and
   d) an interval separating two detected ventricular events that is greater than a second duration, and means for detecting an atrial extrasystole wherein a detected atrial extrasystole is not counted as a detected atrial event,
   wherein said mode commuting means further comprises switching from said AAI pacing mode to said DDD pacing mode in response to any one of said four conditions being met.

2. The device of claim 1, wherein said first number (N1) comprises two.

3. The device of claim 1 wherein said second number (N2) comprises 3 and said third number (N3) comprises 12.

4. The device of claim 1, wherein said fourth number (N4) comprises 6, said first duration separating atrial events and consecutive ventricular detections comprising at least 300 ms in response to an atrial detection, and at least 350 ms in response to an atrial stimulation.

5. The device of claim 1, wherein said second duration comprises 3 seconds.

6. The device of claim 1 wherein said mode commuting means further comprises means for commuting the DDD pacing mode towards the AAI pacing mode in response to a detected spontaneous ventricular activity detected over a number of consecutive cycles, said number being greater than to a fifth number (N5).

7. The device of claim 6 wherein said fifth number (N5) is 12.

8. The device of claim 1, wherein said mode commuting means further comprises means for commuting the DDD pacing mode towards the AAI pacing mode in response to a number of detected ventricular events exceeding a sixth number (N6).

9. The device of claim 8, wherein said sixth number (N6) comprises 100.

10. The device of claim 1, wherein the mode commuting means further comprises means for inhibiting a mode commutation and forcing the operating mode to the DDD pacing mode in response to, during a third duration, a number of commutations of AAI towards DDD than is greater than a seventh number (N7).

11. The device of claim 10, wherein said seventh number (N7) comprises 15, and wherein said third duration comprises 24 hours.

12. The device of claim 1, wherein said mode commuting means further comprises means for inhibiting any commutation of mode and forcing the operating mode to the DDD pacing mode when, during a third duration, the number of commutations of AAI towards DDD during a day is greater than an eighth predetermined number (N8).

13. The device of claim 12, wherein said eighth number (N8) comprises 5 commutations per day, and the third duration comprises three days.

14. The device of claim 1, further comprising means for detecting ventricular extrasystoles, and means for delivering a synchronous atrial stimulation in response to a detected ventricular extrasystole.

15. An active implantable medical device for cardiac rhythm management comprising;
   a detection circuit having an input for receiving signals corresponding to spontaneous atrial and ventricular events and an output identifying spontaneous atrial events, ventricular events and atrial extrasystoles events in said received signals,
   a counter of detected spontaneous atrial events;
   a pulse generator comprising a stimulation circuit able to deliver selectively low energy stimulation pulses to the ventricle and the atrium, said stimulation circuit having an output identifying stimulation pulses as one of a stimulated atrial event and a stimulated ventricular event, said pulse generator being responsive to said detection circuit and having a control circuit comprising a microprocessor, memory and software instructions implementing:
   a DDD pacing mode,
   an AAI pacing mode with a spontaneous ventricular detection, and
   a DDD/AAI stimulation mode monitoring the following four conditions:
   a) a first counted number of consecutive detected atrial events not followed by a detected spontaneous ventricular event that is greater than a first number (N1);
   b) a second counted number of non-consecutive detected sinus atrial events not followed by a detected spontaneous ventricular event that is greater than a second number (N2), said second counted number being counted during a monitoring window comprising a third number (N3) of consecutive detected sinus atrial events;
   c) a third counted number of detected atrial events followed by a detected spontaneous ventricular event occurring after a delay, said delay being greater than a first duration, said third counted number being greater than a fourth value (N4); and
   d) an interval separating two detected ventricular events that is greater than a second duration, wherein a detected spontaneous extrasystole is not counted as a detected atrial event,
   wherein said DDI/AAI stimulation mode further comprises switching from said AAI pacing mode to said DDD pacing mode in response to any of said four conditions being met.

16. The device of claim 15, wherein said first number (N1) comprises two.

17. The device of claim 15 wherein said second number (N2) comprises 3 and said third number (N3) comprises 12.

18. The device of claim 15, wherein said fourth number (N4) comprises 6, and said first duration separating atrial events and consecutive spontaneous ventricular events comprises at least 300 ms in response to a spontaneous atrial event, and at least 350 ms in response to a stimulated atrial event.

19. The device of claim 15, wherein said second duration comprises 3 seconds.

20. The device of claim 15, further comprising a counter of spontaneous ventricular events, wherein said DDD/AAI stimulation mode switches from a DDD pacing mode to a AAI pacing mode in response to a detected spontaneous ventricular activity detected over a number of consecutive cycles, said number being greater than a fifth number (N5).

21. The device of claim 20 wherein said fifth number (N5) is 12.

22. The device of claim 15, further comprising a counter of spontaneous ventricular events, wherein said DDD/AAI stimulation mode switches from a DDD pacing mode to an AAI pacing mode in response to a number of detected ventricular events exceeding a sixth number (N6).

23. The device of claim 22, wherein said sixth number (N6) comprises 100.

24. The device of claim 15, wherein the DDD/AAI stimulation mode reverts to the DDD pacing mode in response to a number of commutations from AAI to DDD during a third duration being greater than a seventh number (N7).

25. The device of claim 24, wherein said seventh number (N7) comprises 15, and wherein said third duration comprises 24 hours.

26. The device of claim 15, wherein DDI/AAI stimulation mode reverts to said DDD pacing mode when, during a third duration, the number of commutations of AAI towards DDD during a day is greater than an eighth predetermined number (N8).

27. The device of claim 26, wherein said eighth number (N8) comprises 5 commutations per day, and the third duration comprises three days.

28. The device of claim 15, further comprising means for detecting ventricular extrasystoles, and means for delivering a synchronous atrial stimulation in response to a detected ventricular extrasystole.

* * * * *